United States Patent
Efinger et al.

(10) Patent No.: US 7,484,709 B2
(45) Date of Patent: Feb. 3, 2009

(54) PRESS-DOWN VALVE FOR MEDICAL INSTRUMENTS FOR SUCTION AND IRRIGATION

(75) Inventors: Andreas Efinger, Rietheim (DE); Michael Riedmüller, Tennenbronn (DE)

(73) Assignee: Karl Storz GmbH & Co. KG (DE)

( * ) Notice: Subject to any disclaimer, the term of this patent is extended or adjusted under 35 U.S.C. 154(b) by 408 days.

(21) Appl. No.: 11/471,368

(22) Filed: Jun. 20, 2006

(65) Prior Publication Data

US 2007/0007479 A1 Jan. 11, 2007

(30) Foreign Application Priority Data

Jun. 20, 2005 (DE) .................. 10 2005 029 756

(51) Int. Cl.
*A61M 39/22* (2006.01)
(52) U.S. Cl. .............. 251/89.5; 251/95; 251/149.9; 604/167.03; 604/246
(58) Field of Classification Search .............. 251/149.9, 251/89.5, 95; 604/164.01, 167.01, 167.03, 604/245–250
See application file for complete search history.

(56) References Cited

U.S. PATENT DOCUMENTS

| | | | | |
|---|---|---|---|---|
| 4,836,199 A * | 6/1989 | Palmer | | 251/95 |
| 5,228,646 A * | 7/1993 | Raines | | 251/95 |
| 5,348,555 A | 9/1994 | Zinnanti | | 606/49 |
| 5,554,112 A | 9/1996 | Walbrink et al. | | 604/27 |
| 5,658,249 A | 8/1997 | Béland et al. | | 604/33 |
| 5,840,016 A * | 11/1998 | Kitano et al. | | 251/335.2 |
| 5,871,441 A | 2/1999 | Ishiguro et al. | | 600/133 |
| 6,364,853 B1 * | 4/2002 | French et al. | | 604/250 |
| 6,447,473 B1 * | 9/2002 | Levine et al. | | 604/249 |

FOREIGN PATENT DOCUMENTS

| | | |
|---|---|---|
| GB | 1 313 353 | 4/1973 |
| JP | 10-52399 | 2/1998 |

OTHER PUBLICATIONS

European Search Report, Oct. 9, 2006, 6 pages.
Karl Storz's Catalog, Endoskope Und Instrumente Fuer HNO, 7. Edition, Feb. 2004, p. 104, 2 pages.

* cited by examiner

*Primary Examiner*—John Bastianelli
(74) *Attorney, Agent, or Firm*—St. Onge Steward Johnston & Reens LLC (57) ABSTRACT

A press-down valve is provided for medical instruments for suction and irrigation and a medical instrument having installed such a press-down valve. A valve stem is pressed permanently into a closure position via a pretensioned spring. For actuation, the valve stem is moved counter to the force of the spring via an actuation element, and, after release, the spring presses the valve stem back into the closure position. A catch mechanism is provided by means of which the valve stem can be locked in the open position only when the press-down valve has been removed from the medical instrument, and that, when it is installed in the medical instrument, the catch mechanism is automatically released and remains released.

36 Claims, 5 Drawing Sheets

Fig.9

PRESS-DOWN VALVE FOR MEDICAL INSTRUMENTS FOR SUCTION AND IRRIGATION

CROSS-REFERENCE TO RELATED APPLICATIONS

The present application claims priority of German patent application No. 10 2005 029 756.0 filed on Jun. 20, 2005, the content of which is incorporated herein by reference.

BACKGROUND OF THE INVENTION

A first design involves a push-button valve with catch function. To start irrigation, the valve button is pushed down and remains in a catch position. To switch the irrigation off, the valve button has to be pushed down again.

In a second design, a so-called press-down valve, irrigation (or, if appropriate, suction) takes place only with the valve button being kept pressed down.

Such a press-down valve forms the subject of the present invention.

In practical use, contaminants can get into the press-down valve, so that it is necessary to clean and sterilize the press-down valve after each use.

To do so, it is customary for the press-down valve to be arranged in a releasable manner on the medical suction and irrigation instrument, so that it can be removed, for example unscrewed, for the cleaning procedure.

Because of their construction, a problem with press-down valves is that the valve stem is always pressed into its closure position. When one wants to clean the press-down valve, it is necessary to activate the valve stem in order to bring the latter into its open position, so that the cleaning liquid can be flushed through the inside of the valve body.

This is extremely difficult to do in the press-down valves, because the spring, pretensioned with quite considerable force, presses the valve stem into the closure position.

It should also be noted that such a press-down valve has dimensions of only a few centimeters, which means that, while holding the press-down valve in one's hand, it is very difficult to keep it in the open position, by pressing the actuation element, and at the same time carry out irrigation.

For construction-related reasons, automated irrigation/cleaning of a press-down valve already dismantled from the medical instrument cannot be performed, because flushing in the open position of the valve stem is not possible. To do this, the press-down valve would have to be installed again in a kind of holder that simulates actuation of the press-down valve, which would be very complicated and extremely laborious.

Therefore, it is an object of the present invention to develop a press-down valve in such a way that it can be easily cleaned.

SUMMARY OF THE INVENTION

The object is achieved by a press-down valve for mounting in a medical instrument for suction and irrigation, comprising a valve stem, a pretensioned spring permanently pressing the valve stem into a closure position closing a flow through the valve, an actuation element which can be activated by one hand and by means of which the valve stem can be moved counter to a force of the spring into an open position, and, after release of the actuation element, the valve stem is moved into the closure position, wherein a catch mechanism is provided by means of which the valve stem can be locked in the open position only when the press-down valve has been removed from a medical instrument, and, when the press-down valve is installed in the medical instrument, the catch mechanism is automatically released and remains released.

The object is further achieved by a medical instrument for suction and irrigation, having a press-down valve comprising a valve stem, a pretensioned spring permanently pressing the valve stem into a closure position closing a flow through the valve, an actuation element which can be activated by one hand and by means of which the valve stem can be moved counter to a force of the spring into an open position, and, after release of the actuation element, the valve stem is moved into the closure position, wherein a catch mechanism is provided by means of which the valve stem can be locked in the open position only when the press-down valve has been removed from the medical instrument, and, when the press-down valve is installed in the medical instrument, the catch mechanism is automatically released and remains released.

This configuration ensures that, as long as the press-down valve is installed in the medical instrument, it remains a press-down valve, i.e. a valve without a locking position. Only when the press-down valve is removed from the instrument is it possible to lock the valve stem in the open position. This can be achieved, for example, by the catch mechanism only being able to be activated in the removed state, not in the installed state. Upon installation in the medical instrument, this catch mechanism is automatically released and remains released, so that the press-down valve in the installed state always retains its function as a press-down valve, that is to say no locking takes place.

After removal of the press-down valve from the instrument, the valve stem can be moved into the open position and locked there, so that the whole inner space of the valve body is accessible to the cleaning fluid for the cleaning procedure. After optional sterilizing, the cleaned press-down valve is fitted back into the medical instrument, whereupon the catch mechanism is released automatically and remains released, thus ruling out the possibility of the press-down valve inadvertently remaining in a locked position when activated. This therefore ensures that, in each installed state, the press-down valve functions exclusively as a press-down valve and not as a lockable valve.

In a further embodiment of the invention, the catch mechanism comprises at least one catch operatively connected to a blocking element by means of which the catch, in the installed state of the press-down valve, is blocked against locking engagement with the valve stem.

This measure has the advantage of ensuring by a mechanically simple measure, namely by the blocking element, that the catch is blocked against locking engagement with the valve stem in the installed state.

In a further embodiment of the invention, the catch of the catch mechanism, in the removed state of the press-down valve, can be brought into the catch position by single activation of the actuation element.

This measure has the advantage of greatly simplifying the handling required for the cleaning procedure. The press-down valve is detached from the medical instrument, and, by pressing the actuation element once, the catch mechanism is brought into the catch position, that is to say the valve stem locks in the open position.

In this position, the press-down valve can then be subjected to a cleaning or sterilizing procedure, which can take place fully automatically for example.

In a further embodiment of the invention, the catch is operatively connected to a release element by means of which the catch can be released.

This measure has the advantage that a release element is specifically provided for releasing the catch when the press-down valve is installed again in the medical instrument. This ensures that the press-down valve, even after a cleaning procedure, again functions as a press-down valve and not as a valve with locking in the medical instrument.

In a further embodiment of the invention, the release element is designed in such a way that, upon installation of the press-down valve into the medical instrument, it releases the catch and leaves it permanently in the released position.

This measure has the advantage that the release element not only releases the catch, but also ensures that the catch remains permanently in the released position as long as the press-down valve is installed in the medical instrument.

In a further embodiment of the invention, the blocking element and release element are formed by one component part.

This measure has the advantage that the additional catch mechanism can be realized using the smallest number of structural elements.

In a further embodiment of the invention, the blocking element can be acted on by a spring force in the direction of a non-blocking position.

This measure has the advantage that, with the press-down valve in the removed state, the blocking element is moved automatically by the spring into a non-blocking position, thus ensuring that the catch mechanism can now act in this state. This opens up the possibility of designing the blocking element such that, upon installation of the press-down valve, the blocking element is displaced counter to the spring force, that is to say in the blocking direction. The aforementioned automatic feature is ensured by very simple mechanical means.

In a further embodiment of the invention, the catch is designed as an elastically resilient element which comes into blocking engagement with an engagement part on the valve stem, as long as the catch is freed from the blocking element and the valve stem is moved into the open position.

This measure has the advantage that the locking can take place without additional handling of the catch. Once the catch is released after removal of the press-down valve from the medical instrument, the catch is as it were already active, and all that needs to be done is for the valve stem to be moved into the open position in order to bring the spring-loaded catch into blocking engagement with the valve stem. By virtue of the spring force, the catch remains in this position throughout the entire cleaning procedure.

In a further embodiment of the invention, the blocking element is designed as an axially extending, spring-loaded pin.

This measure has the advantage that an axially extending blocking element does not constitute a structural element protruding awkwardly from the valve. Moreover, the axial movement during insertion and removal of the press-down valve can equally be used for controlling the blocking element, as the blocking element is displaced correspondingly axially.

In a further embodiment of the invention, the catch is designed as a radially resilient element.

This measure has the advantage that the catch can be installed in the valve body without taking up very much space. By means of the radial path of movement, even just a small radial displacement can create the required mechanically firm engagement for holding the valve stem in its locked position, particularly also for holding it permanently during the entire cleaning procedure.

In a further embodiment of the invention, the pin has, at the end directed toward the resilient element, a bevel which comes into engagement with the radially resilient element upon release of the catch.

This embodiment makes it possible, by means of simple and compact structural elements, to convert the axial movement of the pin across the bevel into a radial disengagement movement of the radially resilient element. This permits a gentle, uniform control of the release of the catch mechanism.

As has already been mentioned, the press-down valves are usually installed with an axial forward movement into the medical element, so that, by axial displacement of the pin of the blocking element, the radially movable, resilient catch element is gradually moved out from the catch position by means of the advancing bevel.

In a further embodiment of the invention, the pin is designed as a pin arranged on the outer face of the valve body.

This measure has the construction-related advantage that no real changes are needed to the dimensions of the valve body, and instead the pin can be arranged on the outer face thereof and, upon insertion of the press-down valve, comes up against a corresponding abutment on the medical instrument, as a result of which the pin is then moved along the outside of the valve body.

In a further embodiment of the invention, the radially resilient element is designed as a radially inwardly pretensioned bar spring.

This measure has the advantage that the catch is designed as a very small structural element that can be easily integrated into the valve body.

In a further embodiment of the invention, a groove is formed in the valve stem, the radially pretensioned bar spring being able to be pressed into blocking engagement in the groove.

This measure has the advantage that, as has already been mentioned, this engagement ensures a permanently fixed locking of the valve stem in its open position. Therefore, the removed press-down valve can also be exposed to mechanical loads during cleaning, flushing, washing and transportation, without any danger of the catch mechanism being released, since the spring-loaded bar spring locked radially in the groove does not escape from the groove, even in the event of mechanical shocks.

In a further embodiment of the invention, the valve stem is received in a valve screw-on piece which has at least two finger molds.

This measure has the advantage that, via the finger molds, the press-down valve can be turned out of the medical instrument by hand, that is to say without using a tool, and, after cleaning, can be reinserted in the same way.

In addition, this measure also contributes to simplifying the cleaning procedure. This embodiment of the finger molds is additionally regarded as an independent invention.

In a further embodiment of the invention, an indented contour of the finger molds is designed in such a way that one mold flank is strongly pronounced in the direction of turning out.

This measure has the advantage that, during turning out, this strongly pronounced mold flank provides a relatively large contact surface for the finger pad, via which contact surface a sufficient tangential pressure can be exerted for turning the press-down valve out. In this way, with this relatively small component part, a sufficient pressure can be exerted by the fingers via the strongly pronounced mold flank in order to dismantle the press-down valve from the medical instrument without the aid of any tools.

In a further embodiment of the invention, the mold flank rises further in the radial direction in the direction of turning out than the opposite mold flank does in the direction of turning in.

This measure has the advantage that the aforementioned greater force or pressure application by the finger is possible in the direction of turning out, whereas, in the opposite direction of turning in, such high pressure cannot be exerted, with the result that the press-down valve does not sit too tightly when inserted and cannot be overtightened.

In the concrete embodiment, the more strongly pronounced mold flank, viewed from the mold depression, extends more steeply and radially farther than the less pronounced mold flank.

In a further embodiment of the invention, the mold flank merges into a peripheral rounding in the direction of turning in.

This measure has the advantage that, once a desired end position has been reached when turning the press-down valve in, the finger, when attempting to turn the press-down valve in farther, moves across the peripheral rounding and in so doing slips out of the mold, so that no further unnecessary forces can be applied.

It will be appreciated that the aforementioned features and those still to be explained below can be used not only in the respectively cited combination, but also in other combinations or singly, without departing from the scope of the present invention.

BRIEF DESCRIPTION OF THE DRAWINGS

The invention is described and explained in more detail below on the basis of a selected illustrative embodiment and in connection with the attached drawings, in which.

DETAILED DESCRIPTION OF THE INVENTION

Figure 1:
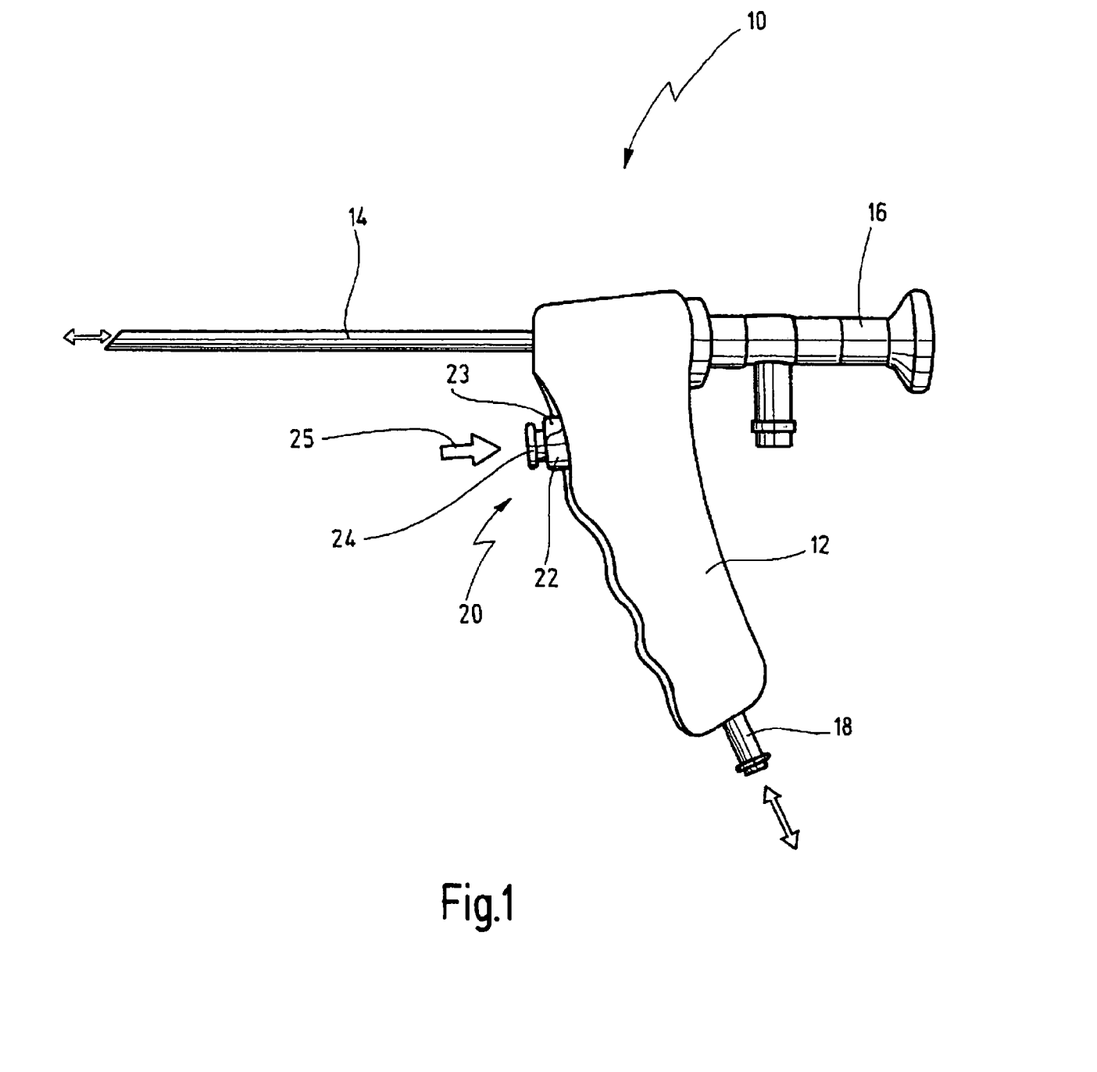
FIG. 1 shows a side view of a medical instrument for suction and irrigation, with a press-down valve according to the invention installed in its grip.

A medical instrument for suction and irrigation, shown in FIG. 1, is designated in its entirety by reference number 10.

The medical instrument 10 has a pistol-like grip 12 which comprises an elongate hollow suction and irrigation shaft 14. An optics system 16 can additionally be fitted in or pushed into the shaft 14, so as to permit visual observation of an operating site in minimally invasive operating procedures, for example. At the outer end of the grip 12 there is a connector piece 18 for connection to a device for suction and irrigation. When carrying out irrigation, an irrigation liquid can be delivered via the connector piece 18, said liquid being guided through lines (not shown here) in the grip 12 to the shaft 14 and then to the distal end thereof, where the irrigation liquid emerges. The irrigation liquid can be used, for example, to flush clear the distal end of the optics system 16, or it can also be used to flush clear the operating site. The irrigation liquid can also be suctioned off again via the shaft 14 and the connector piece 18.

On the distal face of the grip 12, a press-down valve 20 is fitted therein. The press-down valve 20 is connected to the grip 12 via a collar-like screw-on piece 22. Two diametrically opposite finger molds 23 are provided via which the screw-on piece 22 can be gripped with two fingers, for example in order to unscrew the press-down valve 20 from the grip 12.

The press-down valve 20 sits, as is known per se, in the flow path between connector piece 18 and shaft 14.

The press-down valve 20 comprises an actuation element 24 in the form of a button which can be pressed inward counter to the force of a spring, as will be explained in more detail below. When the actuation element 24 is released, the press-down valve 20 shuts off the flow.

When the actuation element 24 is activated as indicated by the arrow 25, for example by a finger of the operating surgeon who is holding the medical instrument 10 in his hand, the press-down valve 20 opens and a flow is permitted, for example the through-flow of an irrigation liquid.

When the actuation element 24 is released, it returns automatically to the blocking position, as a result of the spring force acting on it.

Figure 2:
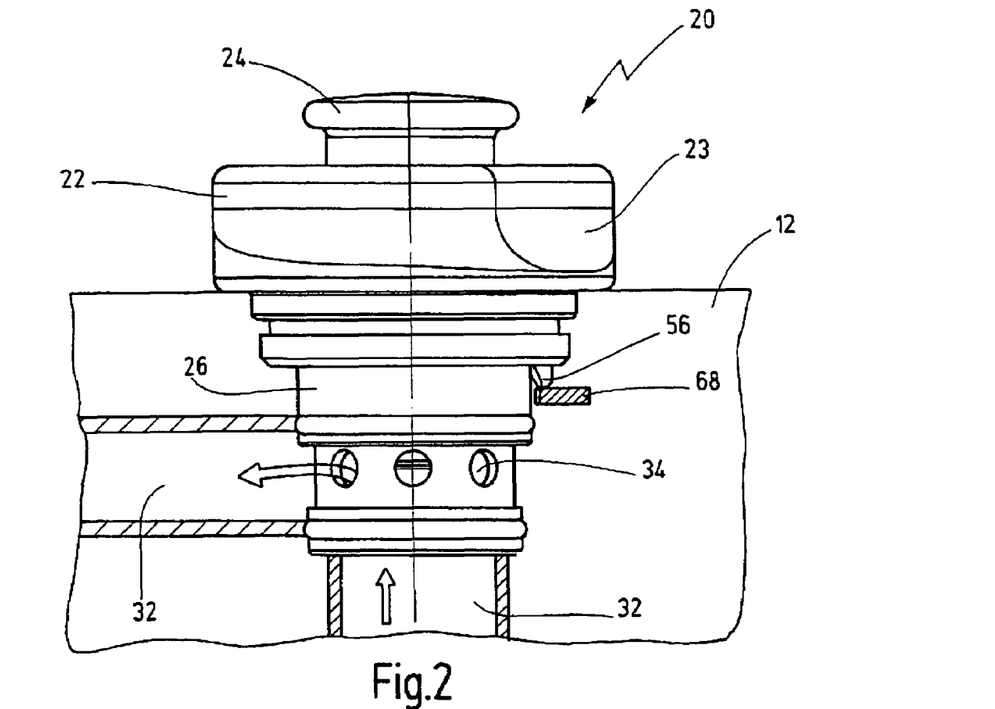
FIG. 2 shows a highly schematic side view of the press-down valve installed in the grip.

FIG. 2 shows the outer contour of the press-down valve 20, the insertion into the line 32 in the inside of the grip 12 being shown only in very diagrammatic form.

It will be seen from FIG. 2 that the screw-on piece 22 can be held by two fingers via the finger moulds 23 in order to turn the press-down valve 20 out of the medical instrument 10 or to fit it into the latter.

Figure 3:
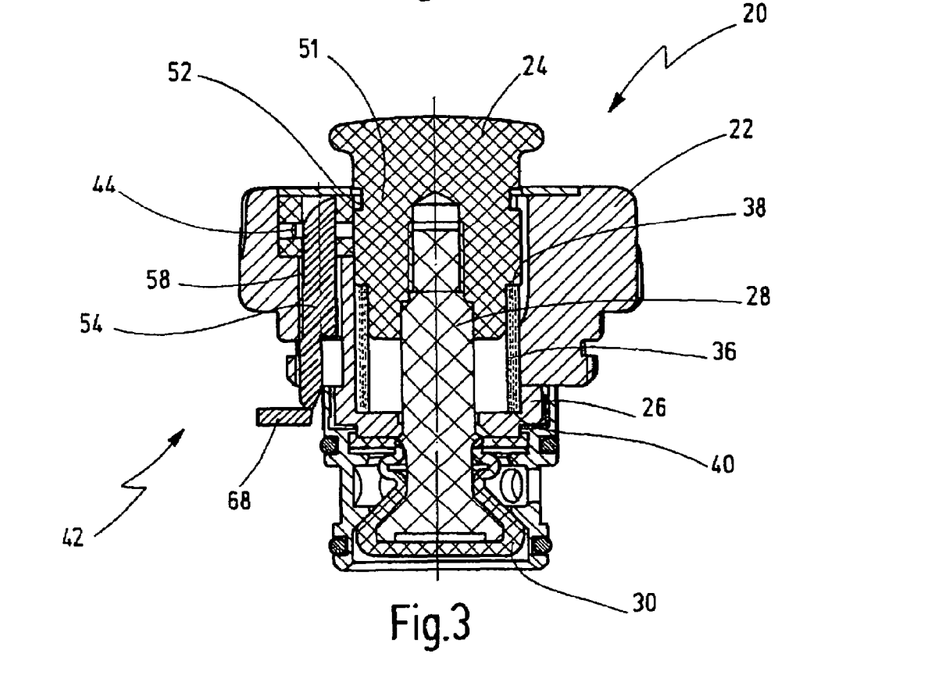
FIG. 3 shows a longitudinal cross section of the press-down valve from FIG. 2, but turned through 180° about its longitudinal axis.

It will be seen from the longitudinal cross-sectional view in FIG. 3 that a valve stem 28 is received in the housing 26. The valve stem 28 is screwed onto the actuation element 24 and forms a single structural unit. At the lower end, the valve stem 28 carries a seal 30 which ensures that a flow through the press-down valve 20 in the direction of the flow arrows in FIG. 2 is blocked. The combined assembly of actuation element 24 and valve stem 28, hereinafter only referred to as valve stem 28, is pretensioned by the force of a spring 36 in such a way that the valve stem 28 is pressed into the closure position shown in FIG. 3. The spring 36 is designed as a helical spring which surrounds the body of the valve stem 28 and bears at one end on a shoulder 38 on the valve stem 28 and at the other end on a ledge 40 of the housing 26.

To open the press-down valve 20, the actuation element 24 is pressed by the finger, as has been described above in connection with FIG. 1, and the valve stem 28 is moved counter to the force of the spring 36 into the open position, so that a flow of irrigation medium or suction medium through the line 32 can then take place. When the actuation element 24 is released again, the valve stem 28 returns to the closure position.

In FIG. 3, the catch mechanism according to the invention is designated in its entirety by reference number 42.

Figure 6:
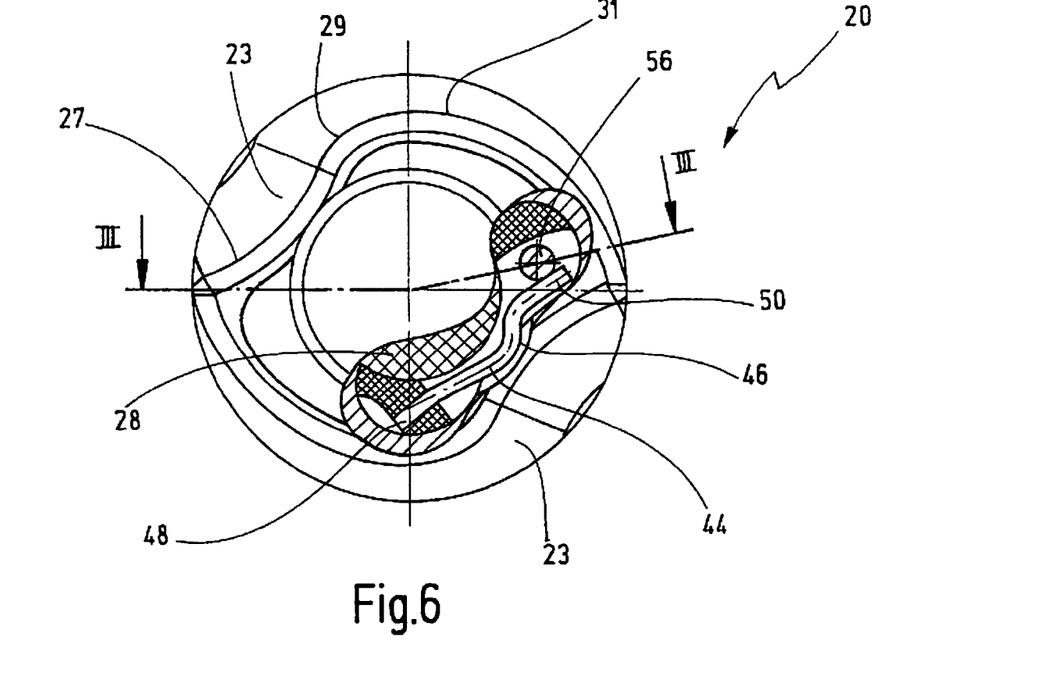
FIG. 6 shows a partially opened plan view of the valve from FIG. 3, in the installed and unlocked state.

The catch mechanism 42 comprises a catch 44 which is arranged in an annular space around the valve stem 28, as can be seen in particular from the cross-sectional view in FIG. 6.

The catch 44 is designed as an S-shaped bar spring 46 whose fixed end 48 is anchored securely in the housing 26, whereas its opposite free end 50 is freely movable, namely radially inward and outward.

In the body of the valve stem 28, in this case in the body 51 of the actuation element 24, a peripheral outer annular groove 52 is formed which is designed in such a way that the free movable end 50 of the catch 44 can enter it when the annular groove 52 comes to lie level with the free end 50 of the S-shaped bar spring 46.

It will be seen from FIGS. 3 and 6 that the catch 44 is locked in the annular groove 52 by a blocking element 54.

The blocking element 54 is designed as a pin 56 which is received in a lateral axial bore in the body of the screw-on piece 22. The pin 56 is acted upon by the force of a spring 58 which extends between an abutment 60 (see FIG. 5 in particular) in the inside of the screw-on piece 22 and a ledge 62 on the pin 56.

The spring 58 is pretensioned in such a way that it tends to move the pin 56 axially downward (in the drawings).

When the press-down valve 20 is installed in the medical instrument 10, as is shown in FIGS. 1 to 3, this movement of the pin 56 is impeded by the fact that the pin 56 rests on an abutment 68 in the inside of the medical instrument.

As can be seen in particular from FIG. 3, when the press-down valve 20 is in this installed state, the pin 56 is displaced axially upward to such an extent that it is located between the free end 50 of the S-shaped bar spring 46 and the body 51 of the valve stem 28. Therefore, in this installed state, the free end 50 is permanently blocked from the S-shaped bar spring 46 of the catch 44 being able to enter the annular groove 52.

Thus, the press-down valve 20 in this state functions as a press-down valve without a locking action.

Figure 4:
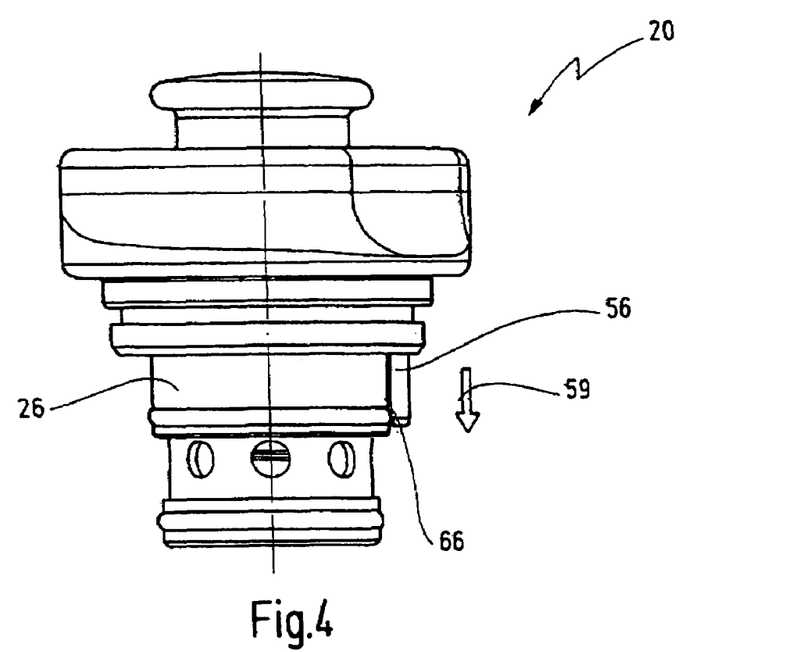
FIG. 4 shows a view of the press-down valve corresponding to FIG. 2, but with the press-down valve having been removed from the instrument.
Figure 5:
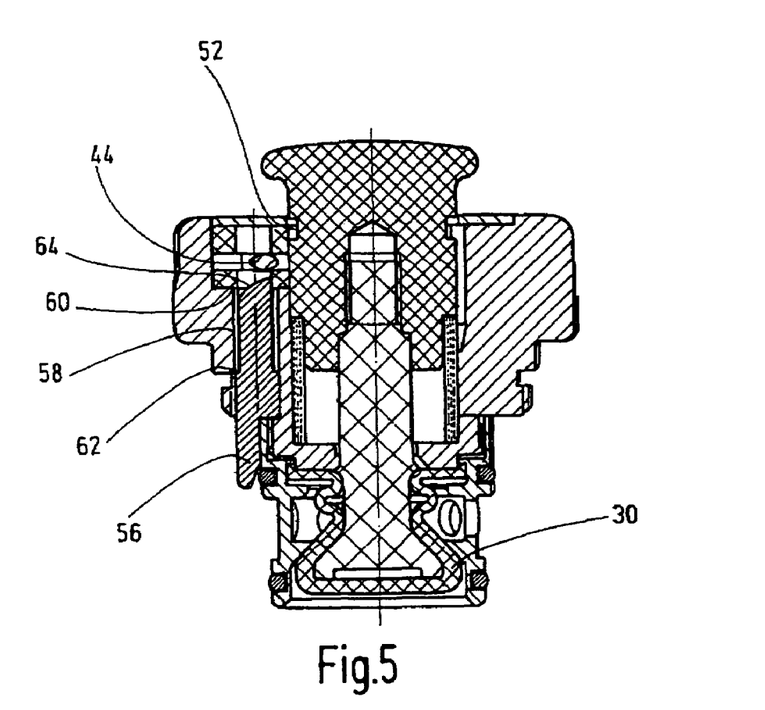
FIG. 5 shows a view comparable to the cross section in FIG. 3, but of the press-down valve in the removed state.

When the press-down valve 20 is now removed from the medical instrument 10, which state is shown in FIGS. 4 and 5, the pin 56 is moved downward by the pretensioned spring 58 until the free end 50 of the S-shaped bar spring 46 is radially freely movable.

It will be seen from the cross-sectional view in FIG. 6 that each finger mold 23 has a somewhat asymmetrical contour. One mold flank 27 is more strongly pronounced than the opposite mold flank 29. The mold flank 27 serves as contact surface for a finger when turning the press-down valve out of the medical instrument 10, this turning movement being counterclockwise. It will be seen from FIG. 6 that the mold flank 27 rises radially further than the opposite mold flank 29. It will also be seen that the mold flank 29 merges into a peripheral rounding 31, which runs gently round as far as the outer peripheral edge.

When turning the press-down valve 20 inward, which is done in the clockwise direction, sufficient force can be exerted via the finger mold 29 to turn the press-down valve 20 inward and secure it, but overtightening is not possible. The reason is that if too much force is applied by the fingers, the finger slips across the gentle rounding 31 out of the finger mold 23, and further turning is not possible.

If, after removal of the press-down valve 20, the actuation element 24 and thus also the valve stem 28 are activated, the annular groove 52 comes to lie before the free end 50 of the catch 44, so that the latter is able to lock in a radially inwardly directed locking movement into the annular groove 52.

Figure 8:
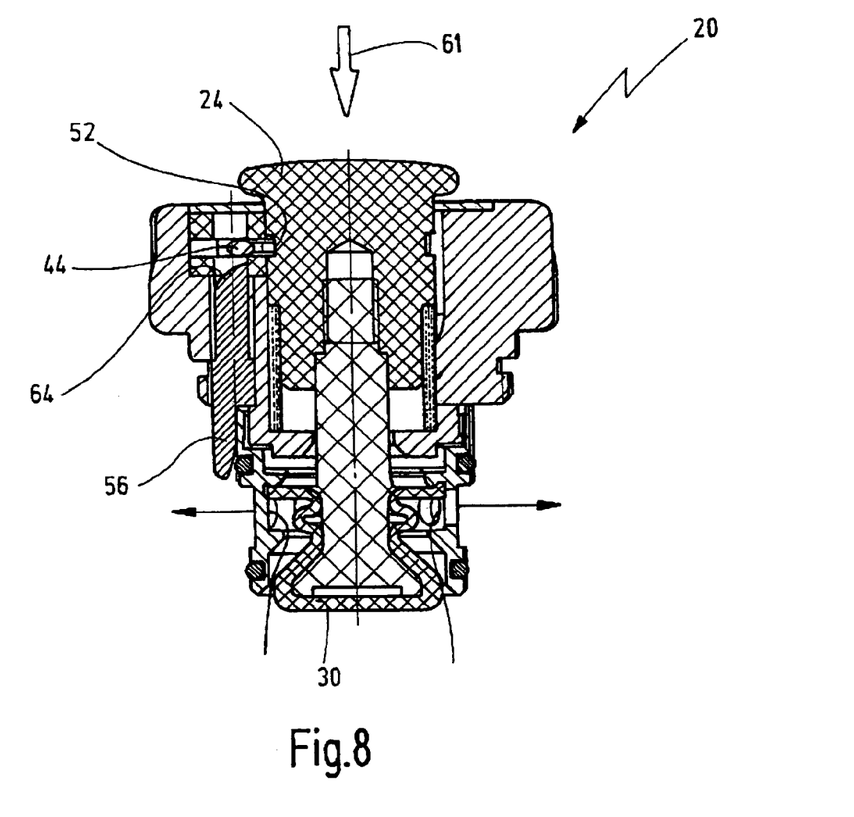
FIG. 8 shows a view of the removed press-down valve, comparable to the view in FIG. 5, after the actuation element has been pressed down once and locked for the cleaning procedure.
Figure 9:
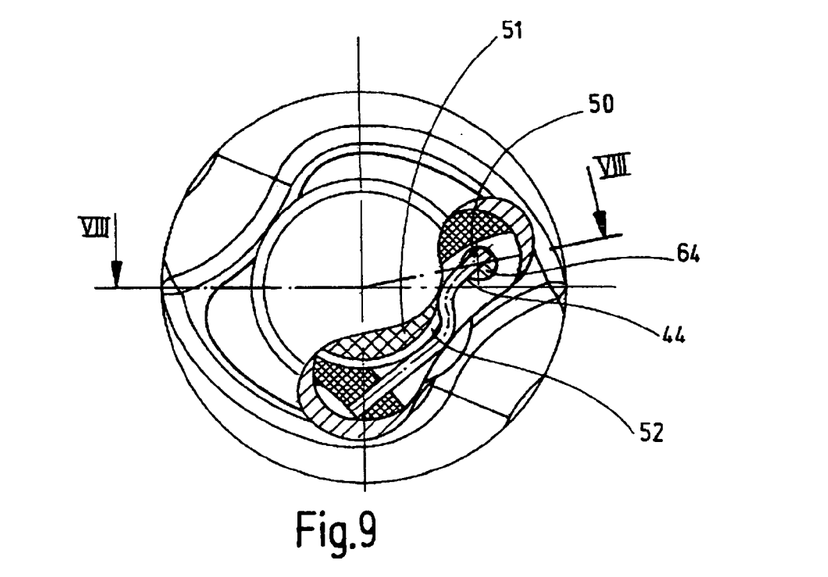
FIG. 9 shows a view comparable to the view in FIG. 7, in the locked state.

This situation is shown in FIGS. 8 and 9.

As is indicated by the arrow 61, the actuation element 24 has been pressed in and the catch 44 is locked into the annular groove 52 and now holds the valve stem 28 in its open position. The seal 30 is lifted from its seat. The whole inner area of the press-down valve 20 coming into contact with the contaminated liquids is now accessible to cleaning fluids in this position, as is indicated by the flow arrows. It will also be seen that the valve stem 28 is held permanently in its open position.

When inserting the press-down valve into the medical instrument 10 after the cleaning, the lower end of the pin 56 as shown in the view in FIG. 8 meets the corresponding abutment 68 (see FIGS. 2 and 3), and, upon further insertion, this pin 56 is displaced upward in the direction of the catch 44. At this end directed toward the catch 44, the pin 56 is provided with a bevel 64.

The bevel 64 is configured such that it comes into engagement with the free end 50 and thus moves this free end 50 radially outward, the catch 44 being moved out of its locking engagement with the groove 52.

Figure 7:
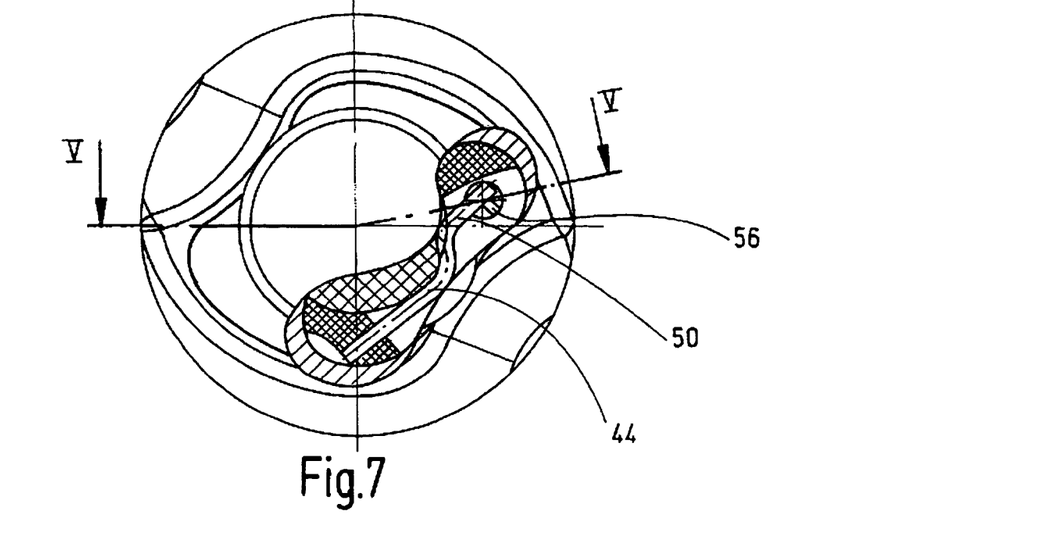
FIG. 7 shows a corresponding view of the valve from FIG. 5, in the removed and locked state.

This changeover is evident, for example, from FIG. 7 to FIG. 6, or the changeover from FIG. 8 to FIG. 3.

Since, as has already been described, the pin 56 of the press-down valve 20 rests on the abutment 68 in the installed state, a movement of the pin 56 in the direction of the force of the spring 58 is no longer possible, such that the blocking element 54 remains permanently in its blocking position, as is shown in FIG. 3. This ensures that, in the installed state, the press-down valve 20 functions exclusively as a press-down valve without blocking.

It will be seen from the views in FIG. 2 and FIG. 4 that the pin 56 is arranged on the outer face 66 of the housing 26 and its free lower end correspondingly comes to lie on the abutment 68 upon insertion.

What is claimed is:

1. A press-down valve for mounting in a medical instrument for suction and irrigation, comprising
   a valve stem;
   a pretensioned spring permanently pressing said valve stem into a closure position closing a flow through said valve;
   an actuation element which can be activated by one hand and by means of which said valve stem can be moved counter to a force of said spring into an open position, and, after release of said actuation element, said valve stem is moved into said closure position; and
   wherein a catch mechanism is provided by means of which said valve stem can be locked in said open position only when said press-down valve has been removed from said medical instrument, and, when said press-down valve is installed in said medical instrument, said catch mechanism is automatically released and remains released.

2. The press-down valve of claim 1, wherein said catch mechanism comprises at least one catch operatively connected to a blocking element by means of which said catch being blocked against locking engagement with that valve stem, if said press-down valve is mounted in said medical instrument.

3. The press-down valve of claim 2, wherein said catch of said catch mechanism, in a state said press-down valve is removed from said medical instrument, can be brought into a catch position by a single activation of said actuation element.

4. The press-down valve of claim 3, wherein said catch is operatively connected to a release element by means of which said catch can be released.

5. The press-down valve of claim 4, wherein said release element is designed in such a way that, upon installation of said press-down valve into said medical instrument, it releases said catch and leaves it permanently in said released position.

6. The press-down valve of claim 5, wherein said release element and said blocking element are formed by one component part.

7. The press-down valve of claim 2, wherein said blocking element is acted on by a spring force in a direction of a non-blocking position.

8. The press-down valve of claim 7, wherein said catch is designed as an elastically resilient element which comes into a blocking engagement with an engagement part of said valve stem, as long as said catch is freed from said blocking element and said valve stem is moved into said open position.

9. The press-down valve of claim 8, wherein said blocking element is designed as an axially extending, spring-loaded pin.

10. The press-down valve of claim 9, wherein said catch is designed as a radially resilient element.

11. The press-down valve of claim 10, wherein a pin has, at an end directed towards to said resilient element, a bevel which comes into engagement with said radially resilient element upon release of said catch.

12. The press-down valve of claim 11, wherein said pin is designed as a pin arranged on an outer face of said valve body.

13. The press-down valve of claim 10, wherein said resilient element is designed as a radially inwardly pretensioned bar spring.

14. The press-down valve of claim 13, wherein a groove is formed in said valve stem, said radially pretensioned bar spring being able to be moved into blocking engagement into said groove.

15. The press-down valve of claim 1, wherein said valve stem is received in a valve screw-on piece which has at least two finger molds.

16. The press-down valve of claim 15, wherein an intended contour of said finger molds is designed in such a way that one mold flank is strongly pronounced in a direction of turning out.

17. The press-down valve of claim 16, wherein said mold flank rises further in a radial direction in a direction of turning out than a opposite mold flank does in a direction of turning in.

18. The press-down valve of claim 17, wherein said mold flank merges into a peripheral rounding in a direction of turning in.

19. A medical instrument for suction and irrigation, having a press-down valve comprising
   a valve stem;
   a pretensioned spring permanently pressing said valve stem into a closure position closing a flow through said valve;
   an actuation element which can be activated by one hand and by means of which said valve stem can be moved counter to a force of said spring into an open position, and, after release of said actuation element, said valve stem is moved into said closure position; and
   wherein a catch mechanism is provided by means of which said valve stem can be locked in said open position only when said press-down valve has been removed from said medical instrument, and, when said press-down valve is installed in said medical instrument, said catch mechanism is automatically released and remains released.

20. The medical instrument of claim 19, wherein said catch mechanism comprises at least one catch operatively connected to a blocking element by means of which said catch being blocked against locking engagement with that valve stem, if said press-down valve is mounted in said medical instrument.

21. The medical instrument of claim 20, wherein said catch of said catch mechanism, in a state said press-down valve is removed from said medical instrument, can be brought into a catch position by a single activation of said actuation element.

22. The medical instrument of claim 21, wherein said catch is operatively connected to a release element by means of which said catch can be released.

23. The medical instrument of claim 22, wherein said release element is designed in such a way that, upon installation of said press-down valve into said medical instrument, it releases said catch and leaves it permanently in said released position.

24. The medical instrument of claim 23, wherein said release element and said blocking element are formed by one component part.

25. The medical instrument of claim 20, wherein said blocking element is acted on by a spring force in a direction of a non-blocking position.

26. The medical instrument of claim 25, wherein said catch is designed as an elastically resilient element which comes into a blocking engagement with an engagement part of said valve stem, as long as said catch is freed from said blocking element and said valve stem is moved into said open position.

27. The medical instrument of claim 26, wherein said blocking element is designed as an axially extending, spring-loaded pin.

28. The medical instrument of claim 27, wherein said catch is designed as a radially resilient element.

29. The medical instrument of claim 28, wherein a pin has, at an end directed towards to said resilient element, a bevel which comes into engagement with said radially resilient element upon release of said catch.

30. The medical instrument of claim 29, wherein said pin is designed as a pin arranged on an outer face of said valve body.

31. The medical instrument of claim 28, wherein said resilient element is designed as a radially inwardly pretensioned bar spring.

32. The medical instrument of claim 31, wherein a groove is formed in said valve stem, said radially pretensioned bar spring being able to be moved into blocking engagement into said groove.

33. The medical instrument of claim 19, wherein said valve stem is received in a valve screw-on piece which has at least two finger molds.

34. The medical instrument of claim 33, wherein an intended contour of said finger molds is designed in such a way that one mold flank is strongly pronounced in a direction of turning out.

35. The medical instrument of claim 34, wherein said mold flank rises further in a radial direction in a direction of turning out than a opposite mold flank does in a direction of turning in.

36. The medical instrument of claim 35, wherein said mold flank merges into a peripheral rounding in a direction of turning in.

* * * * *